United States Patent
Yoshida et al.

(10) Patent No.: US 10,838,512 B2
(45) Date of Patent: Nov. 17, 2020

(54) ELECTRONIC INFORMATION PROCESSING SYSTEM AND STORAGE MEDIUM

(71) Applicant: DENSO CORPORATION, Kariya (JP)

(72) Inventors: Ichiro Yoshida, Kariya (JP); Takafumi Ito, Kariya (JP)

(73) Assignee: DENSO CORPORATION, Kariya (JP)

( * ) Notice: Subject to any disclaimer, the term of this patent is extended or adjusted under 35 U.S.C. 154(b) by 330 days.

(21) Appl. No.: 16/063,816

(22) PCT Filed: Nov. 7, 2016

(86) PCT No.: PCT/JP2016/082964
§ 371 (c)(1),
(2) Date: Jun. 19, 2018

(87) PCT Pub. No.: WO2017/110271
PCT Pub. Date: Jun. 29, 2017

(65) Prior Publication Data
US 2020/0272242 A1    Aug. 27, 2020

(30) Foreign Application Priority Data

Dec. 24, 2015   (JP) ................. 2015-251498

(51) Int. Cl.
| | |
|---|---|
| *G06F 3/023* | (2006.01) |
| *G06F 3/01* | (2006.01) |
| *A61B 5/0476* | (2006.01) |

(52) U.S. Cl.
CPC ............. *G06F 3/023* (2013.01); *G06F 3/015* (2013.01); *G06F 3/018* (2013.01); *A61B 5/0476* (2013.01)

(58) Field of Classification Search
CPC .......... G06F 3/015; G06F 3/023; G06F 3/018; G06F 3/013; G06F 3/0236; G06F 21/32; G06F 3/01; G06F 3/04883; G06F 3/04895
See application file for complete search history.

(56) References Cited

FOREIGN PATENT DOCUMENTS

JP    H05027896 A    2/1993

*Primary Examiner* — Sanjiv D. Patel
(74) *Attorney, Agent, or Firm* — Harness, Dickey & Pierce, P.L.C.

(57) ABSTRACT

In an electronic information processing system, a brain activity detection unit detects an activity of a user's brain. A change determination part determines whether a character input mode presently set needs to be changed to a different character input mode based on a detection result of the brain activity detection unit after a character input under the character input mode presently set is displayed on a display unit. When the change determination part determines that the character input mode presently set needs to be changed to the different character input mode, the character input mode setting part sets the different character input mode instead of the character input mode presently set.

11 Claims, 9 Drawing Sheets

INPUT OF CHARACTERS USER HAS IN MIND

FIG. 7B

INPUT OF CHARACTERS USER DOES NOT HAVE IN MIND

ELECTRONIC INFORMATION PROCESSING SYSTEM AND STORAGE MEDIUM

CROSS REFERENCE TO RELATED APPLICATIONS

This application is a U.S. National Phase Application under 35 U.S.C. 371 of International Application No. PCT/JP2016/082964 filed on Nov. 7, 2016 and published in Japanese as WO 2017/110271 A1 on Jun. 29, 2017. This application is based on and claims the benefit of priority from Japanese Patent Application No. 2015-251498 filed on Dec. 24, 2015. The entire disclosures of all of the above applications are incorporated herein by reference.

TECHNICAL FIELD

The present disclosure relates to an electronic information processing system and a storage medium.

BACKGROUND ART

An electronic information processing system is capable of executing various application programs. In the case of an application program accepting a character input by a user, a character the user does not have in mind may be incorrectly inputted when the user makes a character input operation. For example, in a case where an initial setting of a character input mode is an English one-byte input mode whereas an intent of the user is a hiragana input, an English one-byte character the user does not have in mind may be incorrectly inputted when the user makes a character input operation. In such a case, the user has to go through a tedious procedure: erasing the English one-byte character inputted contrary to the user's intent, changing the character input mode from the English one-byte input mode to a hiragana input mode, and making a hiragana character input operation again.

Patent Literature 1 describes a technique to generate a character code of a character the user intends to input by detecting a time-series change in magnetic field or electric field generated by a function of a brain's language center when the user makes a character input operation.

PRIOR ART LITERATURE

Patent Literature

Patent Literature 1: JP 5-27896 A

SUMMARY OF INVENTION

By applying the technique of Patent Literature 1 to the problem of a tedious procedure the user has to go through, it is expected that a character the user has in mind can be properly inputted. The technique of Patent Literature 1, however, has mainly two difficulties as follows. First, quite a long processing duration is required to input a character the user has in mind because a change in magnetic field or electric field caused by a function of the language center has to be detected in time series. Second, the technique is not suitable to input a large number of characters because only a single character code is generated for one character at a time.

In view of the foregoing difficulties, it is an object of the present disclosure to provide an electronic information processing system and a storage medium each of which is capable of improving a user convenience for inputting characters.

According to an aspect of the present disclosure, a program execution part is configured to execute an application program that accepts an input of a character in at least two different character input modes. An operation acceptance unit accepts a character input operation made by a user. A character input mode setting part sets a character input mode as one of the at least two different character input modes. A display control unit controls a display unit to display a character corresponding to a character input mode presently set by the character input mode setting part when the character input operation made by the user is accepted by the operation acceptance unit during an execution of the application program by the program execution part. A brain activity detection unit detects an activity of a brain of the user. A change determination part determines whether the character input mode presently set by the character input mode setting part needs to be changed to a different character input mode based on a detection result of the brain activity detection unit after the character corresponding to the character input mode presently set is displayed on the display unit under a control of the display control part. The character input mode setting part sets the different character input mode instead of the character input mode presently set when the change determination part determines that the character input mode presently set needs to be changed to the different character input mode.

Attention is paid to a fact that an activity of the user's brain when the user makes a character input operation is different between a case where characters the user has in mind are inputted and a case where characters the user does not have in mind are inputted. When it is determined from a detection result of an activity of the user's brain that the character input mode presently set needs to be changed to a different character input mode, a different character input mode is set instead of the character input mode presently set. Accordingly, when an intent of the user is a character input in the newly set different character input mode, the character input the user has in mind can be performed. Consequently, a character input operation can be more convenient for the user. Different from the related art which uses a time-series change in magnetic field or electric field caused by a function of a brain's language center, the present disclosure uses a difference in activity of the user's brain. Hence, the present disclosure can reduce the processing duration and is therefore suitable to input a large number of characters.

BRIEF DESCRIPTION OF DRAWINGS

The above and other objects, features and advantages of the present invention will become more apparent from the following detailed description made with reference to the accompanying drawings. In the drawings.

EMBODIMENTS FOR CARRYING OUT INVENTION

Figure 1:
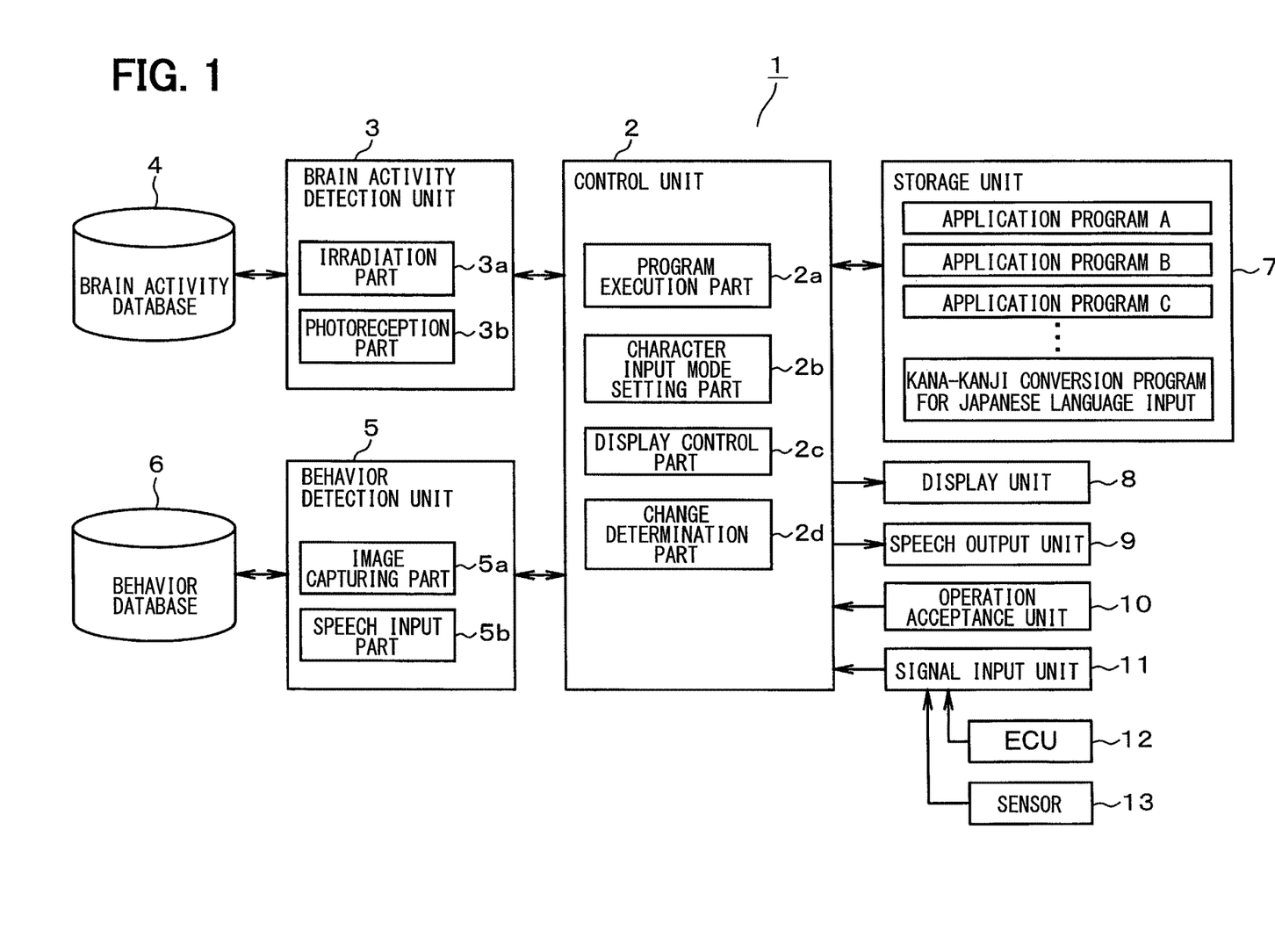
FIG. 1 is a functional block diagram according to one embodiment.

Hereinafter, an electronic information processing system of the present embodiment will be described with reference to the drawings. An electronic information processing system 1 includes a control unit 2, a brain activity detection unit 3, a brain activity database 4, a behavior detection unit 5, a behavior database 6, a storage unit 7, a display unit 8, a speech output unit 9, an operation input unit 10, and a signal input unit 11.

The control unit 2 is provided by a microcomputer having a CPU (Central Processing Unit), a ROM (Read Only Memory), a RAM (Random Access Memory), and IO (Input and Output). By executing a computer program pre-stored in a non-transitory tangible storage medium, the control unit 2 performs process corresponding to the computer program and thereby controls an overall operation of the electronic information processing system 1.

The brain activity detection unit 3 detects an activity of a user's brain by using a NIRS (Near Infra-Red Spectroscopy) technology. In the present embodiment, the user is a driver who drives a vehicle. In information processing by the brain, two systems, namely an information delivery system borne by a neural activity and an energy supply system supporting a neural activity are closely related to each other. At an onset of a neural activity, an adjustment mechanism starts to work by widening peripheral blood vessels to supply more arterial blood containing oxygen and glucose as an energy source. In tissues in close proximity to active nerves, an oxidation state of blood (a ratio of an oxyhemoglobin concentration and a deoxyhemoglobin concentration) is assumed to change with an increase in blood flow and blood volume. A relationship between a neural activity and a brain blood response as above is called neurovascular coupling. In the NIRS technology, an activity of the user's brain is detected by detecting a local hemoglobin concentration at the brain on an assumption that neurovascular coupling is present.

More specifically, the brain activity detection unit 3 includes an irradiation part 3a irradiating near infrared light onto a scalp of the user, and a photoreception part 3b receiving irregularly reflected near infrared light irradiated from the irradiation part. Because near infrared light has high living body penetrability and is therefore capable of passing through a skin and a bone, when near infrared light is irradiated onto a scalp of the user from the irradiation part 3a, optic elements of the near infrared light diffuse into brain tissues and arrive at a cerebral cortex about 20 to 30 millimeters beneath the scalp. By exploiting a property that light absorption characteristics differ between an oxyhemoglobin concentration and a deoxyhemoglobin concentration in blood, optic elements irregularly reflected at a point several centimeters away from an irradiation point are detected by the photoreception part 3b. From the optic elements detected in the manner as above, the brain activity detection unit 3 detects an activity of the user's brain by estimating changes in oxyhemoglobin concentration and deoxyhemoglobin concentration at the cerebral cortex. The brain activity detection unit 3 may detect an activity of the user's brain by estimating a change in total hemoglobin concentration which is a total of the two concentrations in addition to changes in oxyhemoglobin concentration and deoxyhemoglobin concentration at the cerebral cortex.

Each time the brain activity detection unit 3 detects an activity of the user's brain, the brain activity detection unit 3 stores a detection result converted into digital brain activity data into the brain activity database 4. The brain activity detection unit 3 thus updates brain activity data stored in the brain activity database 4 and also checks the newly detected brain activity data against old brain activity data. A comfortable threshold value and an uncomfortable threshold value found from the brain activity data stored in the brain activity database 4 are preliminarily set in the brain activity detection unit 3 and used as determination references. When a numerical value of the brain activity data is equal to or greater than the comfortable threshold value, the brain activity detection unit 3 detects that the user feels comfortable. When a numerical value of the brain activity data is less than the comfortable threshold value and equal to or greater than the uncomfortable threshold value, the brain activity detection unit 3 detects that the user feels normal (neither comfortable nor uncomfortable). When a numerical value of the brain activity data is less than the uncomfortable threshold value, the brain activity detection unit 3 detects that the user feels uncomfortable. The brain activity detection unit 3 outputs a detection result signal indicating a detection result of an activity of the user's brain detected in the manner above to the control unit 2. The brain activity detection unit 3 may constantly detect an activity of the user's brain or start a detection on condition that a detection start command signal is inputted from the control unit 2 and end the detection on condition that a detection end command signal is inputted from the control unit 2.

The behavior detection unit 5 detects a behavior of the user by using image analysis and speech recognition techniques. More specifically, the behavior detection unit 5 includes an image capturing part 5a capturing an image of an upper half of the user including a face, and a speech input part 5b inputting a speech uttered by the user. The behavior detection unit 5 captures an image of motion of eyes (visual line), motion of a mouth (utterance of a speech), and an expression of the user by using the image capturing part 5a, and inputs a speech uttered by the user by using the speech input part 5b. The behavior detection unit 5 detects a behavior of the user by identifying a change in motion of the eyes, motion of the mouth, and expression of the user, and speech uttered by the user. The behavior detection unit 5 may detect a behavior of the user from at least one of motion of the eyes, motion of the mouth, an expression, and a speech uttered by the user, or may detect a behavior of the user by combining two or more of the foregoing factors.

Each time the behavior detection unit 5 detects a behavior of the user, the behavior detection unit 5 stores a detection result converted into digital behavior data into the behavior database 6. The behavior detection unit 5 thus updates behavior data stored in the behavior database 6 and also checks the newly detected behavior data against old behavior data. The behavior detection unit 5 sets a comfortable threshold value and an uncomfortable threshold value based on the behavior data stored in the behavior database 6, and the comfortable threshold value and the uncomfortable threshold value are used as determination references. When a numerical value of the behavior data is equal to or greater than the comfortable threshold value, the behavior detection unit 5 detects that the user feels comfortable. When a numerical value of the behavior data is less than the comfortable threshold value and equal to or greater than the uncomfortable threshold value, the behavior detection unit 5 detects that the user feels normal (neither comfortable nor uncomfortable). When a numerical value of the behavior data is less than the uncomfortable threshold value, the behavior detection unit 5 detects that the user feels uncomfortable. The behavior detection unit 5 outputs a detection result signal indicating a detection result of a behavior of the user detected in the manner above to the control unit 2. The behavior detection unit 5 may constantly detect a behavior of the user, or start a detection on condition that a detection start command signal is inputted from the control unit 2 and end the detection on condition that a detection end command signal is inputted from the control unit 2.

The storage unit 7 has stored multiple programs executable by the control unit 2. Programs stored in the storage unit 7 include an application program capable of accepting a character input in multiple character input modes, and a kana-kanji conversion program for Japanese language input (corresponding to a character conversion program for predetermined language input). The kana-kanji conversion program for Japanese language input is software by which kana-kanji conversion is performed to input a Japanese sentence, and is also called a Japanese language input program, a Japanese language input front end processor (FEP for short), and a kana-kanji conversion program. The character input modes include an English one-byte input mode, an English two-byte input mode, a katakana one-byte input mode, a katakana two-byte input mode, a hiragana input mode, and so on.

The display unit 8 is provided by, for example, a liquid crystal display. Upon input of a display command signal from the control unit 2, the display unit 8 displays a screen image specified by the display command signal inputted. The speech output unit 9 is provided by, for example, a speaker. Upon input of a speech output command signal from the control unit 2, the speech output unit 9 outputs a speech specified by the speech output command signal inputted. The operation input unit 10 is provided by a touch panel provided onto a screen of the display unit 8, mechanical switches, and so on. Upon detection of an operation by the user, the operation input unit 10 outputs an operation detection signal indicating a content of the operation to the control unit 2. The touch panel is provided with multiple character keys the user can depress. The signal input unit 11 inputs various signals from various ECUs (Electronic Control Units) 12 and various sensors 13 equipped to the vehicle.

The control unit 2 includes a program execution part 2a, a character input mode setting part 2b, a display control part 2c, and a change determination part 2d. The respective parts 2a through 2d are provided by computer programs executed by the control unit 2 and implemented by software. The program execution part 2a executes various programs stored in the storage unit 7. While an application program is in execution, the program execution part 2a also starts the kana-kanji conversion program for Japanese language input when the character input mode set in the application program in execution is the hiragana input mode. That is, by also starting the kana-kanji conversion program for Japanese language input when the hiragana input mode is set, the program execution part 2a makes a kana character input available and further enables kana-kanji conversion (conversion from kana characters to kanji characters).

Figure 2:
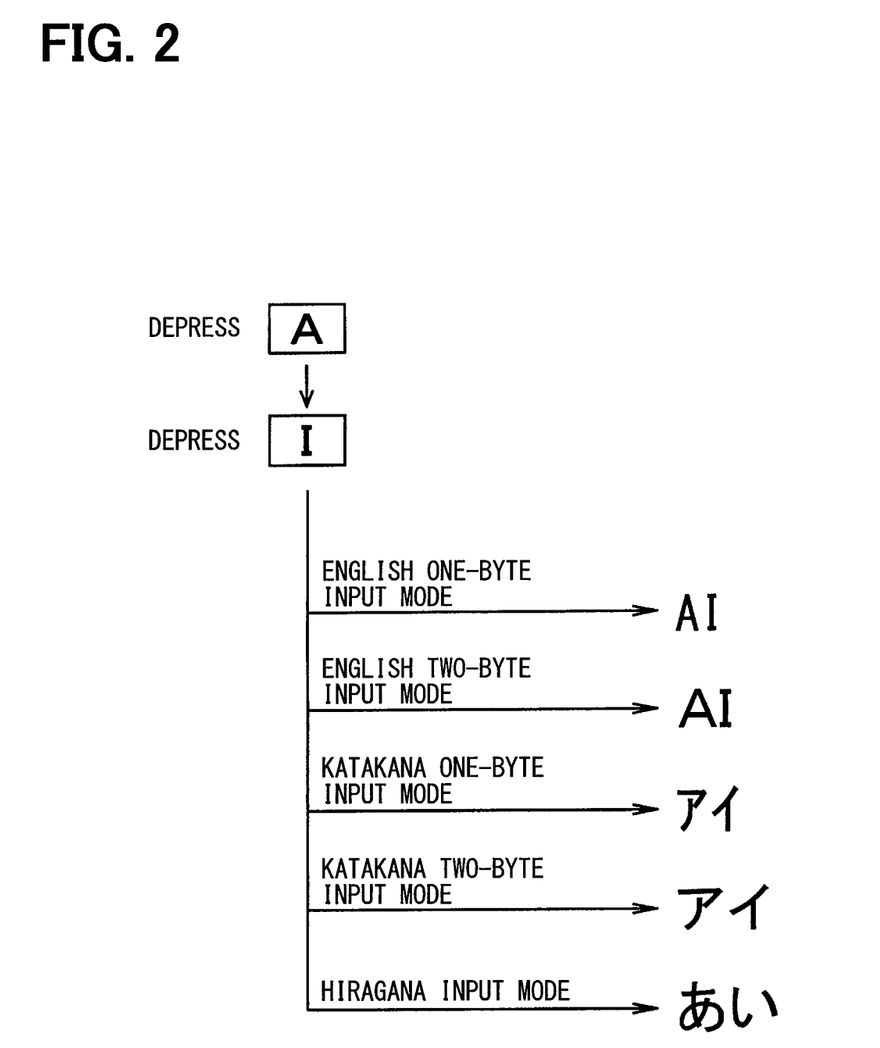
FIG. 2 is a view showing how characters are inputted.

The character input mode setting part 2b sets one of the multiple character input modes specified above. The display control part 2c controls the display unit 8 to display a character corresponding to the character input mode set by the character input mode setting part 2b on a character display region when a character input operation by the user is accepted at the operation acceptance unit 10 while an application program is being executed by the program execution part 2a. That is, as is shown in FIG. 2, when the user makes a character input operation by depressing a key "A" first and thence a key "I", the display control part 2c controls the display unit 8 to display characters as follows. When the English one-byte input mode is set, the display control part 2c controls the display unit 8 to display "AI" in half-width alphabet. When the English two-byte input mode is set, the display control part 2c controls the display unit 8 to display "AI" in full-width alphabet. When the katakana one-byte input mode is set, the display control part 2c controls the display unit 8 to display "ｱｲ (katakana characters of A and I)" in half-width katakana. When the katakana two-byte input mode is set, the display control part 2c controls the display unit 8 to display "アイ (katakana characters of A and I)" in full-width katakana. When the hiragana input mode is set, the display control part 2c controls the display unit 8 to display "あい (hiragana characters of A and I)" in full-width hiragana. Although it will be described in detail below, the change determination part 2d determines whether the character input mode presently set needs to be changed to a different character input mode by using a detection result of the brain activity detection unit 3 and a detection result of the behavior detection unit 5.

A function of the configuration described above will now be described with reference to FIG. 3 through FIG. 9. An example described in the following is a case where the character input mode is changed from, for example, the English one-byte input mode to the hiragana input mode. That is, in a case where a user who wishes a hiragana input makes a character input operation while an application program set in the English one-byte input mode as the initial setting of the character input mode is in execution, and feels uncomfortable with an English one-byte character inputted as a result.

Figure 3:
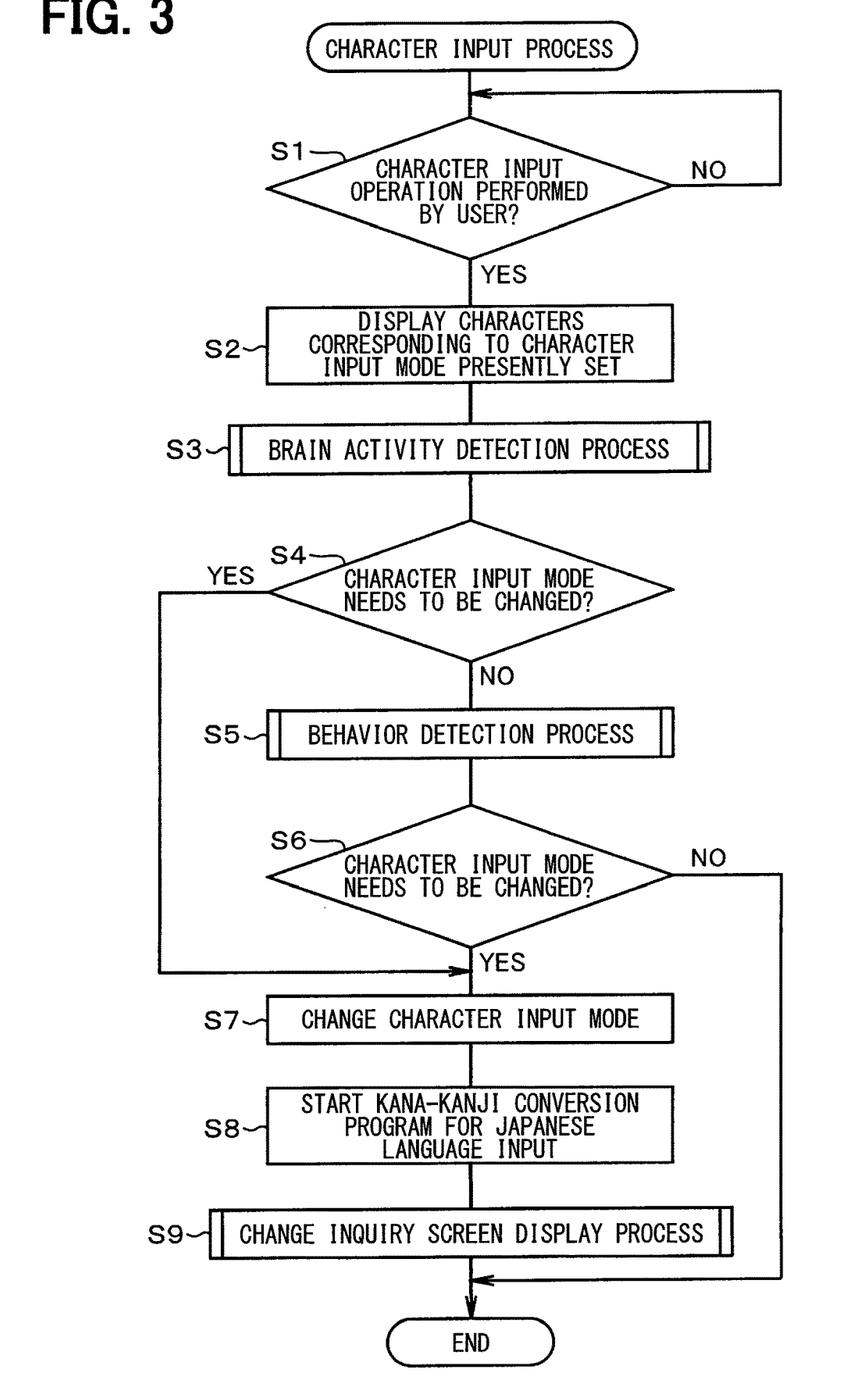
FIG. 3 is a flowchart (part 1)

In the electronic information processing system 1, the control unit 2 monitors a character input operation by the user once character input process is started (S1). When the control unit 2 determines that a character input operation by the user is accepted (S1: YES) in response to an input of an operation detection signal from the operation acceptance unit 10, the control unit 2 controls the display unit 8 to display characters corresponding to the character input mode set at a present moment (S2). That is, the user is enabled to determine whether characters the user has in mind are correctly inputted by visually confirming characters displayed on the display unit 8. The control unit 2 then proceeds to brain activity detection process (S3, corresponding to a first step).

Figure 4:
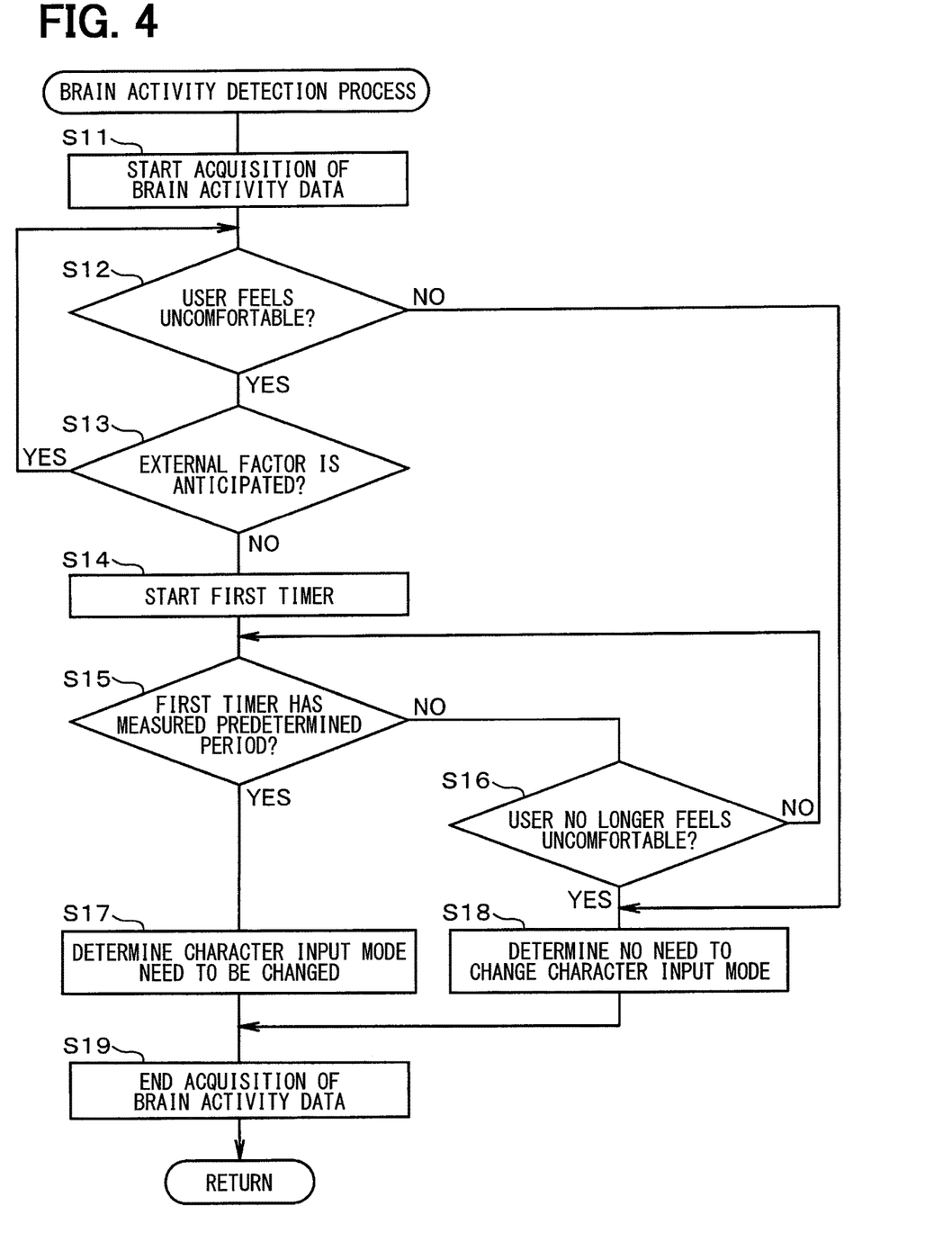
FIG. 4 is a flowchart (part 2)

After the control unit 2 starts the brain activity detection process, the control unit 2 starts to acquire brain activity data converted from a detection result signal inputted from the brain activity detection unit 3 (S11). The control unit 2 acquires the brain activity data in every predetermined period (for example, every several milliseconds), and determines an activity of the user's brain at a present moment, that is, a feeling of the user immediately after the user visually confirms the characters displayed on the display unit 8 (S12). When an intent of the user is the English one-byte input, the character input mode matches the intent of the user. Hence, the user visually conforms that characters the user has in mind are inputted. In such a circumstance, the user's brain does not become active and a brain activity changes little. The user therefore feels comfortable or normal and does not feel uncomfortable.

Figure 7A:
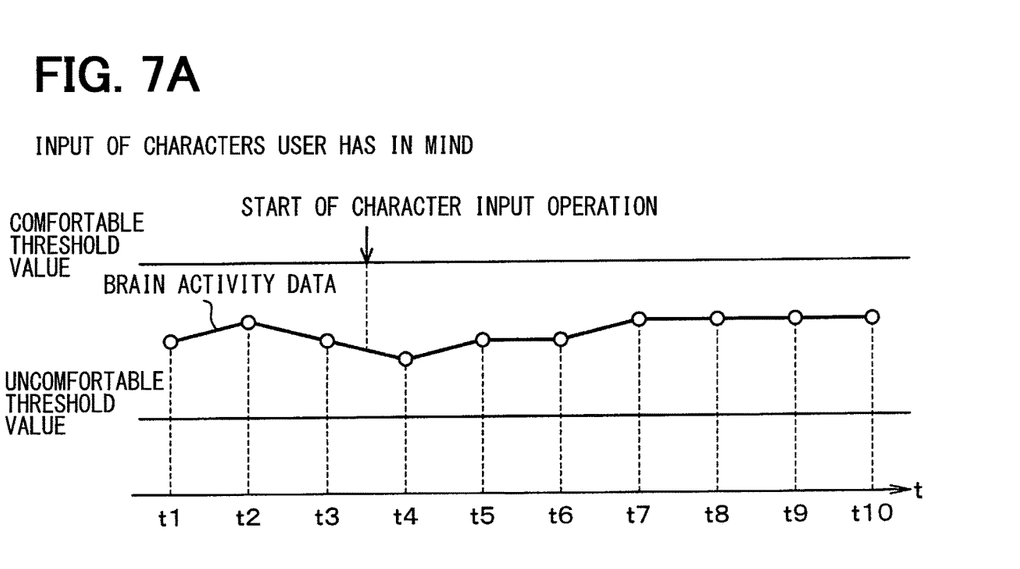
FIG. 7A is a view (part 1) showing a change in brain activity data.

When the control unit 2 determines that the user does not feel uncomfortable based on a numerical value of the brain activity data that is not less than the uncomfortable threshold value (S12: NO), the control unit 2 determines that the character input mode does not need to be changed (S18). Hence, the control unit 2 ends acquisition of the brain activity data (S19) and ends the brain activity detection process. That is, as is shown in FIG. 7A, when characters the user has in mind are inputted, a numerical value of the brain activity data does not decrease below the uncomfortable threshold value. Hence, the control unit 2 determines that the character input mode does not need to be changed and ends the brain activity detection process.

Meanwhile, when an intent of the user is an input other than the English one-byte input, for example, the hiragana input, the character input mode presently set does not match the intent of the user. Hence, the user visually confirms that characters the user does not have in mind are inputted. In such a circumstance, the user's brain becomes active and shows a change. The user therefore feels uncomfortable. When the control unit 2 determines that the user feels uncomfortable because a numerical value of the brain activity data is less than the uncomfortable threshold value (corresponding to a first predetermined state) (S12: YES), the control unit 2 determines whether an external factor is anticipated (S13). The external factor is, for example, a change in environment the user is in. That is, in a case where timing when the user makes a character input operation falls exactly on timing when a change occurs in the environment the user is in, the user does not feel uncomfortable with a character input operation but may possibly feel uncomfortable temporarily due to a change in environment the user is in. In order to eliminate such a case, when the control unit 2 determines that an external factor is anticipated (Step S13: YES), the control unit 2 returns to Step S12 and repeats Step S12 and subsequent steps. A change in environment the user is in may be an abrupt change in a vehicle state, such as an abrupt change in acceleration and vibration applied to the vehicle. The control unit 2 determines whether an external factor is anticipated by determining whether the environment the user is in has changed by using various signals inputted from the various ECUs 12 and the various sensors 13 through the signal input unit 11.

Figure 7B:
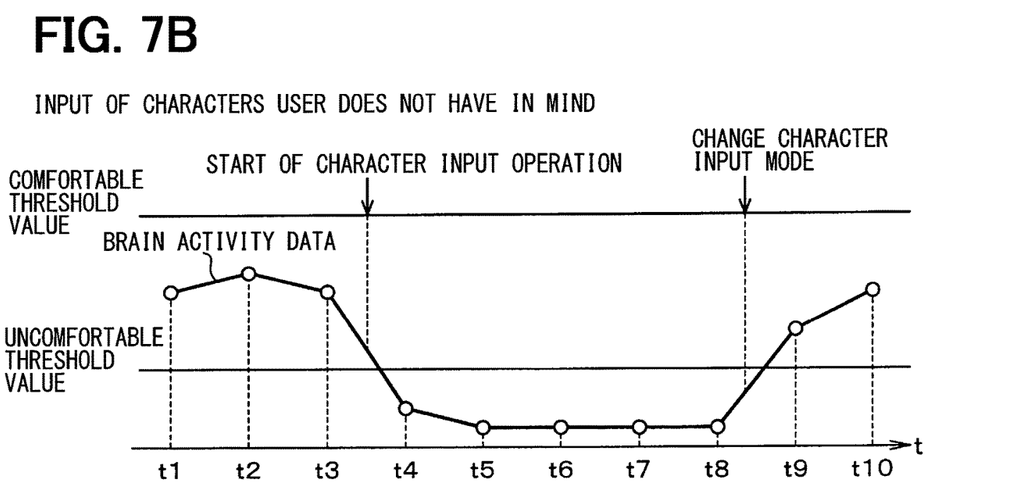
FIG. 7B is a view (part 2) showing a change in brain activity data.

When the control unit 2 determines that no external factor is anticipated (S13: NO), the control unit 2 starts a first timer which measures a first predetermined period (for example, several seconds) (S14). The control unit 2 then monitors whether the first timer has measured the first predetermined period (S15) while monitoring whether the user no longer feels uncomfortable (S16). When the control unit 2 determines that the timer has measured the first predetermined period while the user still feels uncomfortable, that is, a state in which the user feels uncomfortable continues for the predetermined period (S15: YES), the control unit 2 determines that the character input mode needs to be changed (S17). Hence, the control unit 2 ends acquisition of the brain activity data (S19) and ends the brain activity detection process. That is, as is shown in FIG. 7B, when characters the user has in mind are not inputted, a numerical value of the brain activity data decreases below the uncomfortable threshold value, and a state in which the user feels uncomfortable continues for the predetermined period. Hence, the control unit 2 determines that the character input mode needs to be changed and ends the brain activity detection process.

When the control unit 2 determines that the user no longer feels uncomfortable before the first timer measures the first predetermined period (S16: YES), the control unit 2 determines that the character input mode does not need to be changed (S18). Hence, the control unit 2 ends acquisition of the brain activity data (S19) and ends the brain activity detection process.

After the control unit 2 ends the brain activity detection process, the control unit 2 determines whether the character input mode needs to be changed as a determination result of the brain activity detection process (S4, corresponding to a second step). When the control unit 2 determines that the character input mode needs to be changed (S4: YES), the control unit 2 changes the character input mode from the English one-byte input mode to the hiragana input mode (S7, corresponding to a third step). The control unit 2 also starts the kana-kanji conversion program for Japanese language input (S8). After the character input mode is changed from the English one-byte input mode to the hiragana input mode and the kana-kanji conversion program for Japanese language input is also started in the manner as above, the user can input characters in the hiragana input mode from a present moment. Meanwhile, when the control unit 2 determines that the character input mode does not need to be changed (S4: NO), the control unit 2 proceeds to behavior detection process (S5, corresponding to a fourth step).

Figure 5:
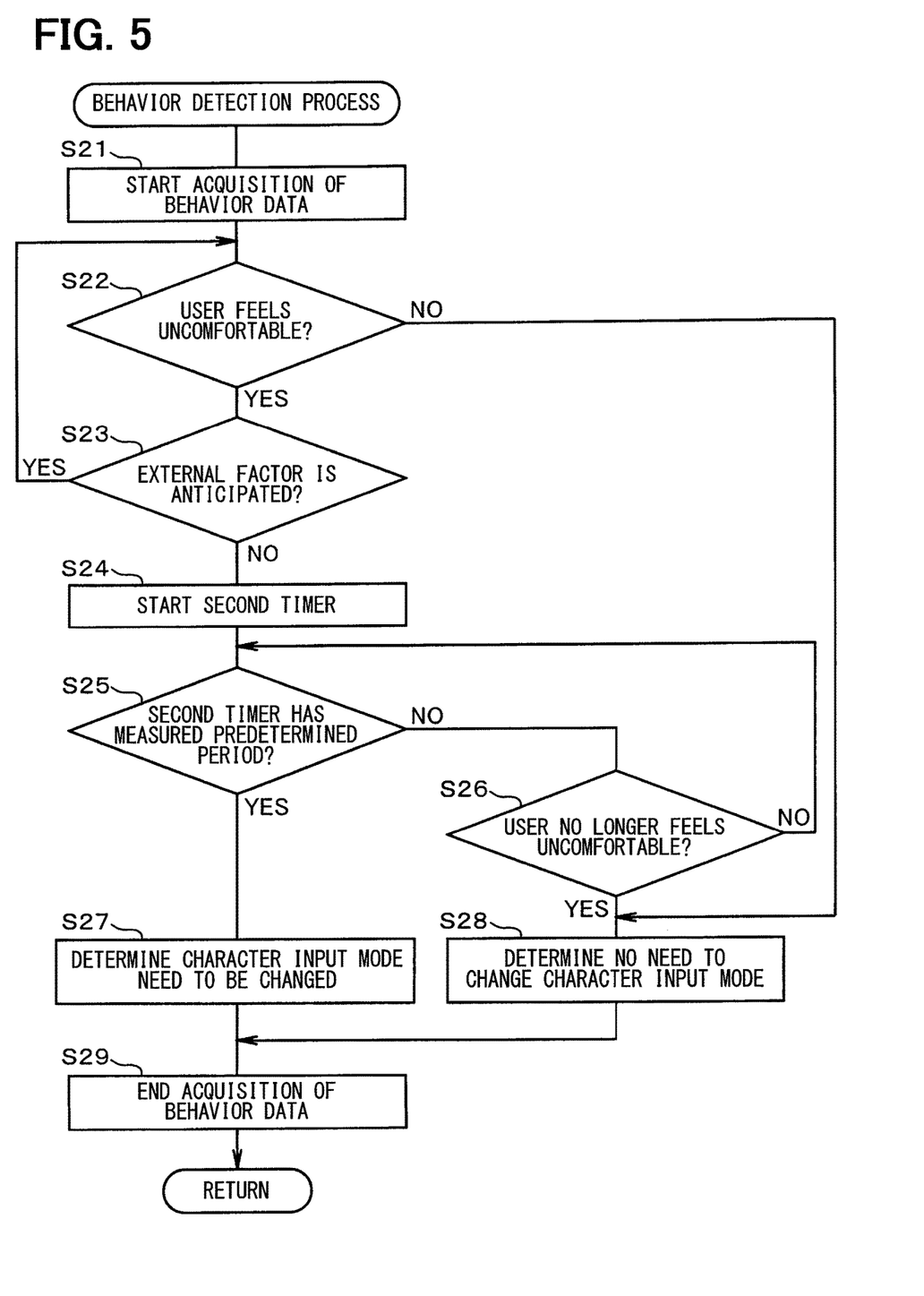
FIG. 5 is a flowchart (part 3)

After the control unit 2 starts the behavior detection process, the control unit 2 starts to acquire behavior data converted from a detection result signal inputted from the behavior detection unit 5 (S21). The control unit 2 acquires the behavior data in every predetermined period (for example, every several milliseconds), and determines a behavior of the user at a present time, that is, a feeling of the user immediately after the user visually confirms characters displayed on the display unit 8 (S22). In the present process, too, when an intent of the user is the English one-byte input, the character input mode presently set matches the intent of the user and the user visually confirms that characters the user has in mind are inputted. In such a circumstance, a behavior of the user is normal and stable. The user therefore feels comfortable or normal and does not feel uncomfortable.

Figure 8A:
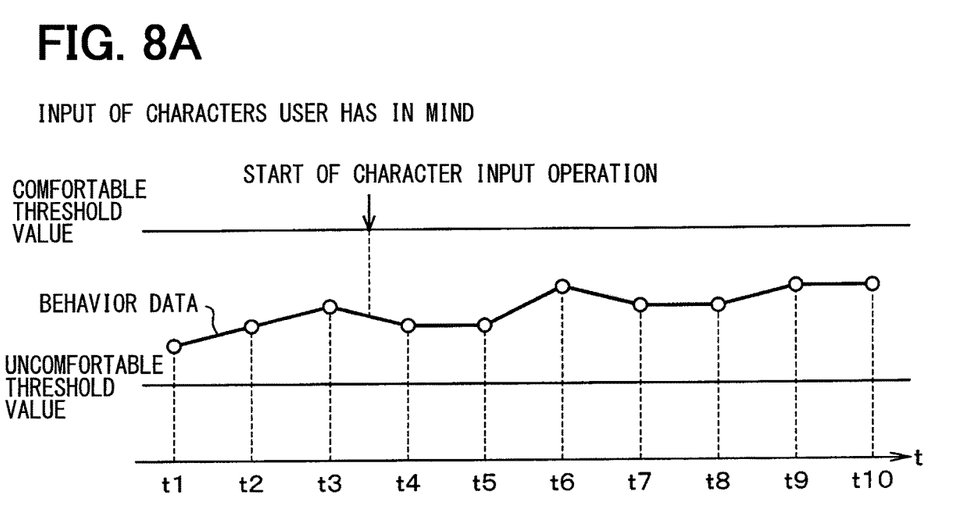
FIG. 8A is a view (part 1) showing a change in behavior data.

When the control unit 2 determines that the user does not feel uncomfortable because a numerical value of the behavior data is not less than the uncomfortable threshold value (S22: NO), the control unit 2 determines that the character input mode does not need to be changed (S28). Hence, the control unit 2 ends acquisition of the behavior data (S29) and ends the behavior detection process. That is, as is shown in FIG. 8A, when characters the user has in mind are inputted, a numerical value of the behavior data does not decrease below the uncomfortable threshold value. Hence, the control unit 2 determines that the character input mode does not need to be changed and ends the behavior detection process.

Meanwhile, when an intent of the user is an input other than the English one-byte input, for example, the hiragana input, the character input mode presently set does not match the intent of the user. Hence, the user visually confirms that characters the user does not have in mind are inputted. In such a circumstance, for example, the user's eyes move rapidly or an expression of the user changes noticeably, that is, a behavior of the user is different from a normal behavior and becomes unstable. The user therefore feels uncomfortable.

Figure 8B:
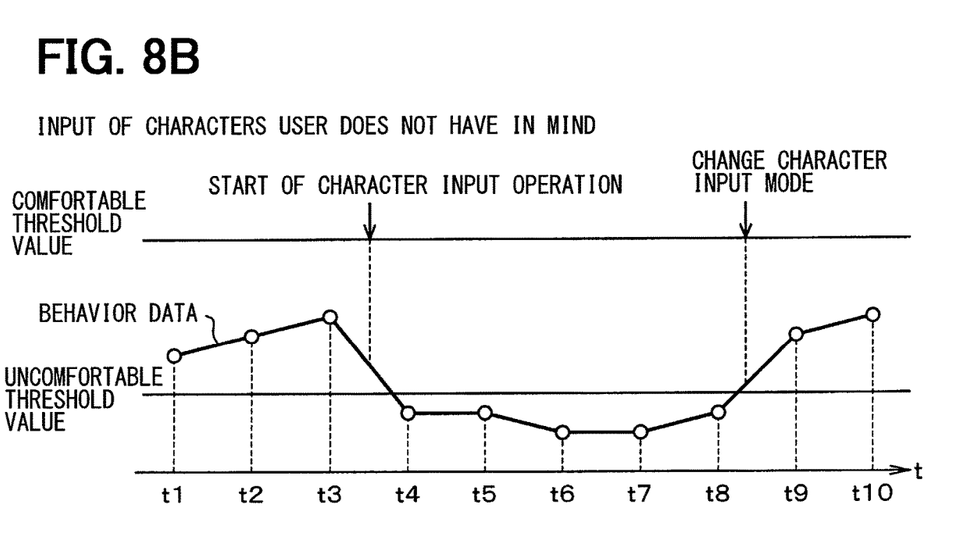
FIG. 8B is a view (part 2) showing a change in behavior data.

When the control unit 2 determines that the user feels uncomfortable because a numerical value of the behavior data is less than the uncomfortable threshold value (corresponding to a second predetermined state) (S22: YES), the control unit 2 determines whether an external factor is anticipated (S23). When the control unit 2 determines that an external factor is anticipated (Step S23: YES), the control unit 2 returns to Step S22 and repeats Step S22 and subsequent steps. When the control unit 2 determines that no external factor is anticipated (S23: NO), the control unit 2 starts a second timer which measures a second predetermined period (for example, several seconds) (S24). The control unit 2 then monitors whether the second timer has measured the second predetermined period (S25) while monitoring whether the user no longer feels uncomfortable (S26). When the control unit 2 determines that the second timer has measured the second predetermined period while the user still feels uncomfortable, that is, a state in which the user feels uncomfortable continues for the predetermined period (S25: YES), the control unit 2 determines that the character input mode needs to be changed (S27). Hence, the control unit 2 ends acquisition of the behavior data (S29) and ends the behavior detection process. That is, as is shown in FIG. 8B, when characters the user has in mind are not inputted, a numerical value of the behavior data decreases below the uncomfortable threshold value and a state in which the user feels uncomfortable continues for the predetermined period. Hence, the control unit 2 determines that the character input mode needs to be changed and ends the behavior detection process.

When the control unit 2 determines that the user no longer feels uncomfortable before the second timer measures the second predetermined period (S26: YES), the control unit 2 determines that the character input mode does not need to be changed (S27). Hence, the control unit 2 ends acquisition of the behavior data (S29) and ends the behavior detection process.

After the control unit 2 ends the behavior detection process, the control unit 2 determines whether the character input mode needs to be changed as a determination result of the behavior detection process (S6, corresponding to a fifth step). When the control unit 2 determines that the character input mode needs to be changed (S6: YES), the control unit 2 changes the character input mode from the English one-byte input mode to the hiragana input mode (S7, corresponding to a sixth step). The control unit 2 also starts the kana-kanji conversion program for Japanese language input (S8).

After the control unit 2 changes the character input mode from the English one-byte input mode to the hiragana input mode and also starts the kana-kanji conversion program for Japanese language input in the manner as above, the control unit 2 proceeds to change inquiry window display process (S9). Meanwhile, when the control unit 2 determines that the character input mode does not need to be changed (S6: NO), the control unit 2 ends the character input process without changing the character input mode.

Figure 6:
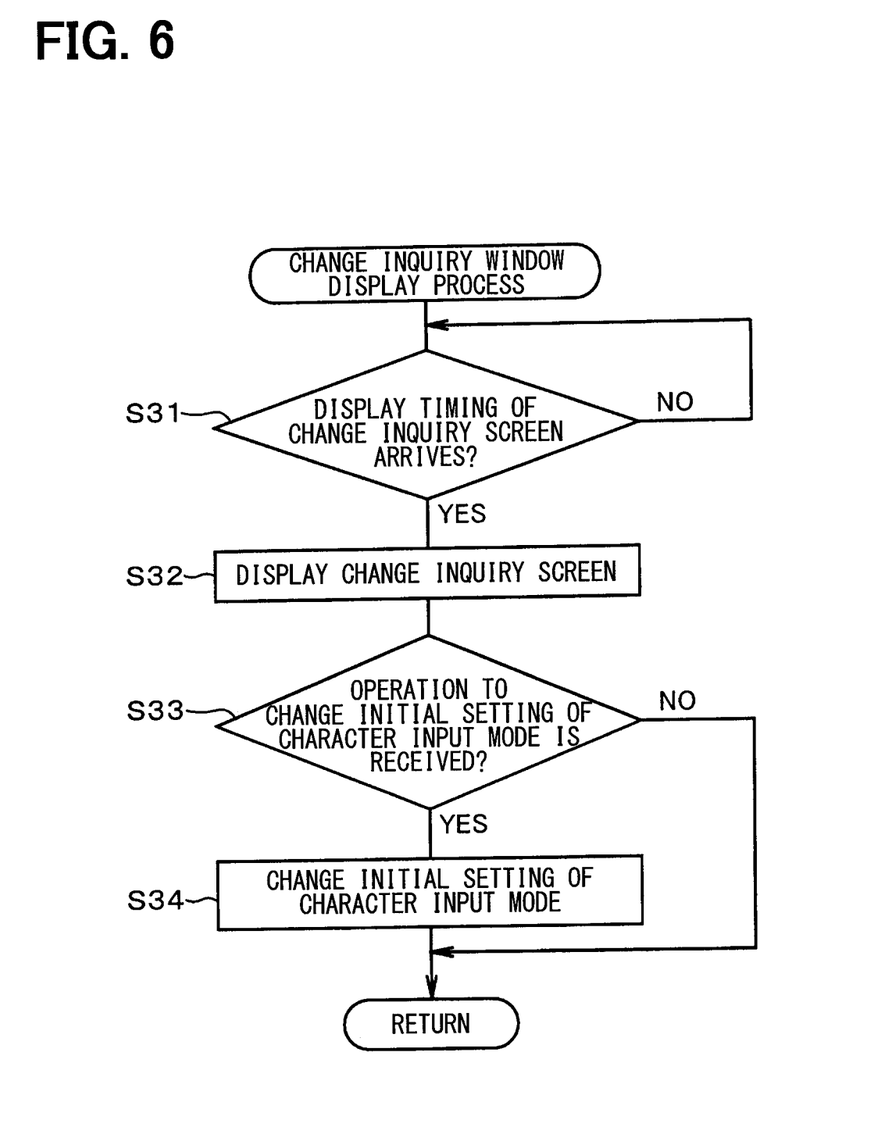
FIG. 6 is a flowchart (part 4)
Figure 9:
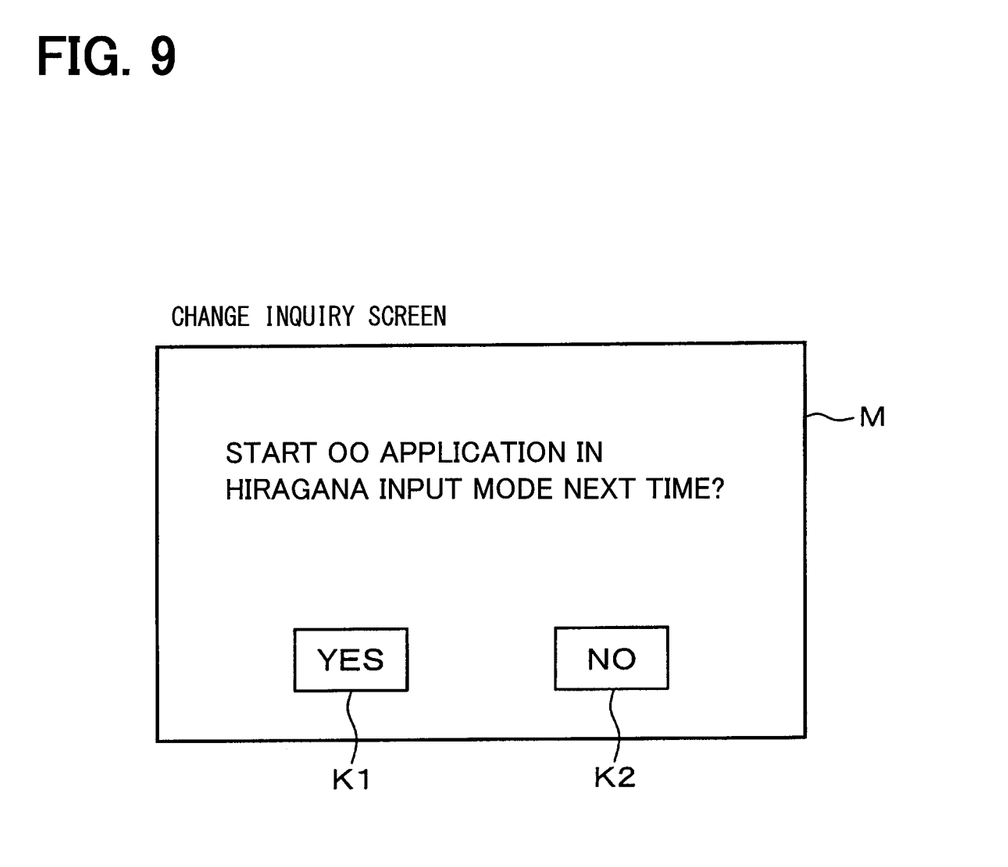
FIG. 9 is a view showing a change inquiry window.

After the control unit 2 starts the change inquiry window display process, the control unit 2 determines whether a display timing of a change inquiry window arrives (S31). When the control unit 2 determines that display timing of the change inquiry window arrives (S31: YES), the control unit 2 controls the display unit 8 to display a change inquiry window M as is shown in FIG. 9 (S32). The control unit 2 inquires about whether to change the initial setting of the character input mode, that is, whether to start the application program in question in the hiragana input mode next time, through the change inquiry window M, and waits for a reply from the user (S33). When the control unit 2 determines that the user has made an operation to change the initial setting of the character input mode (that is, permits a change of the initial setting) by depressing a "YES" key K1 on the change inquiry window M (S33: YES), the control unit 2 changes the initial setting of the character input mode (S34) and ends the change inquiry window display process. When the user permits a change of the initial setting in the manner as above, the control unit 2 sets the hiragana input mode as the initial setting of the character input mode next time the control unit 2 starts the application program in question. Meanwhile, when the control unit 2 determines that the user has not made an operation to change the initial setting of the character input mode (that is, inhibits a change of the initial setting) by depressing a "NO" key K2 on the change inquiry window M (S33: NO), the control unit 2 ends the change inquiry window display process without changing the initial setting of the character input mode. When the user inhibits a change of the initial setting as above, the control unit 2 maintains the English one-byte input mode as the initial setting of the character input mode next time the control unit 2 starts the application program in question.

In the case described above, the control unit 2 starts the kana-kanji conversion program for Japanese language input by changing the English one-byte input mode to the hiragana input mode. Alternatively, the control unit 2 does not have to start the kana-kanji conversion program for Japanese language input in a case where the character input mode is changed to a different input mode other than the hiragana input mode. One character input mode can be changed to another character input mode in any combination. When the hiragana input mode is changed to a different character input mode, the kana-kanji conversion program for Japanese language input in execution may be deactivated. The control unit 2 may always change the character input mode to a specific character input mode set in advance by an operation by the user when the user feels uncomfortable or the control unit 2 may learn which character input mode is set when the user does not feel uncomfortable.

With the above-described configuration, effects as follows can be obtained by.

In the electronic information processing system 1, attention is paid to a fact that an activity of the user's brain when the user makes a character input operation is different between a case where characters the user has in mind are inputted and a case where characters the user does not have in mind are inputted. When it is determined from a detection result of an activity of the user's brain that the character input mode presently set needs to be changed, a different character input mode is set instead of the character input mode presently set. Accordingly, when an intent of the user is a character input in the different character input mode newly set, character input the user has in mind can be performed. Consequently, this configuration improves a convenience for user's input operation of the characters.

In the electronic information processing system 1, it is determined that the character input mode needs to be changed when a detection result of an activity of the user's brain shows that a period during which the user feels uncomfortable continues for the first predetermined period. A determination made according to a detection result of an activity of the user's brain may possibly have an error that the user who does not feel uncomfortable is determined as feeling uncomfortable due to a noise or the like. Such an error can be avoided by the configuration above.

In the electronic information processing system 1, attention is paid to a fact that not only an activity of the user's brain, but also to a behavior of the user, such as motion of the eyes and an expression of the user, when the user makes a character input operation is different between a case where character the user has in mind are inputted and a case where characters the user does not have in mind are inputted. Whether the character input mode presently set needs to be changed is determined by using a detection result of a behavior of the user. When it is determined that the character input mode needs to be changed, a different character input mode is set instead of the character input mode presently set. Accordingly, when an intent of the user is a character input in the different character input mode newly set, character input the user has in mind can be performed. Consequently, this configuration improves a convenience for user's input operation of the characters.

In the electronic information processing system 1, it is determined that the character input mode needs to be changed when a detection result of a behavior of the user shows that a period during which the user feels uncomfortable continues for the second predetermined period. A determination made according to a detection result of a behavior of the user may possibly have an error that the user who feels comfortable is determined as feeling uncomfortable due to a noise or the like. Such an error can be avoided by the configuration above, too.

In the electronic information processing system 1, when the character input mode is changed to the hiragana input mode, the kana-kanji conversion program for Japanese language input is also started. Accordingly, not only a hiragana input is made available, but also conversion from hiragana characters to kanji characters may be enabled. Consequently, a character input operation by Japanese language input can be far more convenient. In addition, in the electronic information processing system 1, the user can select whether to change the initial setting of the character input mode next time a same application program is started. By changing the initial setting of the character input mode next time the application program is started, an uncomfortable feeling that the user has otherwise can be avoided when the application program is started next time.

While the disclosure has been described with reference to preferred embodiments thereof, it is to be understood that the disclosure is not limited to the preferred embodiments and constructions. The disclosure is intended to cover various modification and equivalent arrangements. In addition, the various combinations and configurations, which are preferred, other combinations and configurations, including more, less or only a single element, are also within the spirit and scope of the disclosure.

The configuration of the present disclosure is not limited to vehicle-mounted applications and can be also adopted for applications other than vehicle-mounted applications.

In the present embodiment, both of a detection result of the brain activity detection unit 3 and a detection result of the behavior detection unit 5 are used. Alternatively, whether to change the character input mode may be determined by using a detection result of the brain activity detection unit 3 alone. In short, a detection result of the behavior detection unit 5 may be used when needed.

In the present embodiment, the NIRS technology is used as a technique to detect an activity of the user's brain. Instead of the NIRS technology, other technologies may be used.

What is claimed is:

1. An electronic information processing system comprising:
a program execution part configured to execute an application program that accepts an input of a character in at least two different character input modes;
an operation acceptance unit accepting a character input operation made by a user;
a character input mode setting part setting a character input mode as one of the at least two different character input modes;
a display control unit controlling a display unit to display a character corresponding to a character input mode presently set by the character input mode setting part when the character input operation made by the user is accepted by the operation acceptance unit during an execution of the application program by the program execution part;
a brain activity detection unit detecting an activity of a brain of the user; and
a change determination part determining whether the character input mode presently set by the character input mode setting part needs to be changed to a different character input mode based on a detection result of the brain activity detection unit after the character corresponding to the character input mode presently set is displayed on the display unit under a control of the display control part,
wherein the character input mode setting part sets the different character input mode instead of the character input mode presently set when the change determination part determines that the character input mode presently set needs to be changed to the different character input mode.

2. The electronic information processing system according to claim 1, wherein:
the change determination part determines that the character input mode presently set needs to be changed to the different character input mode when the detection result of the brain activity detection unit indicates that an activity of the brain of the user continuously maintains a first predetermined state for a first predetermined period.

3. The electronic information processing system according to claim 1, further comprising:
a behavior detection unit detecting a behavior of the user, wherein the change determination part determines whether the character input mode presently set by the character input mode setting part needs to be changed to the different character input mode based on the detection result of the brain activity detection unit and a detection result of the behavior detection unit after the character corresponding to the character input mode presently set is displayed on the display unit under the control of the display control part.

4. The electronic information processing system according to claim 3, wherein:
the change determination part determines that the character input mode presently set needs to be changed to the different character input mode when the detection result of the brain activity detection unit indicates that an activity of the brain of the user continuously maintains in a first predetermined state for a first predetermined period or the detection result of the behavior detection unit indicates that a behavior of the user continuously maintains in a second predetermined state for a second predetermined period.

5. The electronic information processing system according to claim 1, wherein:
the program execution part is configured to execute a character conversion program prepared for a predetermined language input in addition to the application program; and
the program execution part starts the character conversion program prepared for the predetermined language input when the different character input mode is set by the character input mode setting part instead of the character input mode presently set.

6. The electronic information processing system according to claim 5, wherein:
the program execution part starts a kana-kanji conversion program prepared for Japanese language input as the character conversion program prepared for the predetermined language input.

7. The electronic information processing system according to claim 1, wherein:
when the different character input mode is set by the character input mode setting part instead of the character input mode presently set during the execution of the application program, the program execution part is configured to set the different character input mode as an initial setting of the character input mode next time the program execution part starts the application program.

8. The electronic information processing system according to claim 7, wherein:
in response to a permission of a change of the initial setting from the user, the program execution part sets the different character input mode as the initial setting of the character input mode next time the program execution part starts the application program.

9. The electronic information processing system according to claim 7, wherein:
in response to an inhibition of a change of the initial setting from the user, the program execution part maintains the character input mode presently set as the initial setting of the character input mode next time the program execution part starts the application program.

10. A non-transitory tangible computer readable storage medium comprising a computer program, wherein the computer program comprising instructions for controlling a control unit included in an electronic information processing system to execute an application program and control a display unit to display a character when a character input operation made by a user is accepted by an operation acceptance unit during an execution of the application program, the application program accepts the character input operation in at least two different character input modes and the character input by the user is displayed corresponding to a character input mode presently set,
the instructions for executing:
detecting an activity of a brain of the user with a brain activity detection unit after the character input by the user under the character input mode presently set is displayed on the display unit;
determining whether the character input mode presently set needs to be changed to a different character input mode based on a detection result of the detecting of the activity of the brain of the user; and
setting the different character input mode instead of the character input mode presently set when determining that the character input mode presently set needs to be changed to the different character input mode.

11. The storage medium according to claim 10, further comprising instructions of the computer program for:
detecting a behavior of the user with a behavior detection unit after the character input by the user under the character input mode presently set is displayed on the display unit when determining that the character input mode presently set does not need to be changed to the different character input mode;
determining whether the character input mode presently set needs to be changed to the different character input mode based on a detection result of the detecting of the behavior of the user; and
setting the different character input mode instead of the character input mode presently set when determining that the character input mode presently set needs to be changed to the different character input mode.

* * * * *